(12) United States Patent
Jamali et al.

(10) Patent No.: US 8,772,227 B2
(45) Date of Patent: Jul. 8, 2014

(54) GLUCOSAMINE PRO-DRUG

(71) Applicants: Fahkreddin Jamali, Edmonton (CA); Kamalijit Kaur, Edmonton (CA); Mohammadhossien Gilzad, Edmonton (CA)

(72) Inventors: Fahkreddin Jamali, Edmonton (CA); Kamalijit Kaur, Edmonton (CA); Mohammadhossien Gilzad, Edmonton (CA)

( * ) Notice: Subject to any disclaimer, the term of this patent is extended or adjusted under 35 U.S.C. 154(b) by 0 days.

(21) Appl. No.: 13/622,516

(22) Filed: Sep. 19, 2012

(65) Prior Publication Data

US 2013/0196897 A1  Aug. 1, 2013

Related U.S. Application Data

(63) Continuation-in-part of application No. 13/410,615, filed on Mar. 2, 2012, now abandoned.

(60) Provisional application No. 61/448,247, filed on Mar. 2, 2011.

(51) Int. Cl.
*A61K 47/48* (2006.01)

(52) U.S. Cl.
CPC ..... *A61K 47/48038* (2013.01); *A61K 47/48246* (2013.01)

USPC ................ 514/1.3; 536/55; 536/53; 530/322; 514/62

(58) Field of Classification Search
None
See application file for complete search history.

(56) References Cited

FOREIGN PATENT DOCUMENTS

EP     0653434 A1  *  5/1995  ............. C07H 15/12

OTHER PUBLICATIONS

Wang et al. J Rheumatology. 34(4);712-720:2007.*

* cited by examiner

*Primary Examiner* — Karlheinz R Skowronek
*Assistant Examiner* — Schuyler Milton
(74) *Attorney, Agent, or Firm* — William J. Bundren

(57) ABSTRACT

To develop glucosamine (GlcN) pro-drugs with properties superior to the presently available GlcN products, we have synthesized derivatives with improved pharmaceutical properties. The synthesized derivatives include peptide-GlcN ester and amide conjugates where the peptide portion consists of one or more amino acids. One such compound is (5-amino-3,4,6-trihydroxyoxan-2-yl)methyl 2-(2-aminoacetamido)-3-methylbutanoate or glycine-valine-COO-GlcN (GV-GlcN).7.

4 Claims, 7 Drawing Sheets

GLUCOSAMINE PRO-DRUG

BACKGROUND

Glucosamine (GlcN) is a naturally occurring amino-sugar that has been used to treat various ailments including osteoarthritis (OA). Animal studies suggest potent anti-inflammatory and disease modifying effects for GlcN. The reported human clinical trials are, however, inconclusive (1-10). In addition, plasma GlcN concentration following effective doses (~300 mg/kg) (11,12,13) to the rat are several magnitudes greater than those expected or observed following human doses (1500 mg/day) (13). Similarly, GlcN plasma concentrations of products with beneficial effects in the treatment of OA (14), although variable, are substantially higher that those with no or negligible effects (13).

We hypothesized that pro-drugs of GlcN and other amino-sugars such as butyryl glucosamine will possess relatively high bioavailability that yield high concentrations, hence, will be effective against OA and rheumatoid arthritis (RA). Therefore, developing pro-drugs that yield high bioavailability of GlcN or butyryl glucosamine is beneficial.

We attribute the controversial results of various studies to the following points:
(a) GlcN is not a regulated compound, hence, the quality of the available products and also those used in clinical trials are questionable. It has been reported that except for one, all commercially available products contain substantially less GlcN than the label claim (15).
(b) The dosing regimens used are empiric because of scant pharmacologic information. A dose-effect study using a pharmaceutical grade GlcN formulation is lacking. Indeed, clinical trials have typically concentrated on a 1500 mg/day (label claim, very likely <1500 mg/day) regimen. Only animal studies and human trials that have been carried out with relatively high doses or were associated with high plasma GlcN concentrations have reported pharmacological efficacy. GlcN has a low and erratic bioavailability following oral doses, hence, excessively large doses are needed for desired effects.
(c) Due to its physical instability, GlcN is often crystallised along with considerable amount of KCl, hence, a typical tablets containing 500 mg GlcN weighs around 1.4 g. The mere size of the available tablets deters patients from taking these pills more than 500 mg t.i.d. to experience the beneficial effects of higher amount in the body.

SUMMARY OF INVENTION

Figure 4:
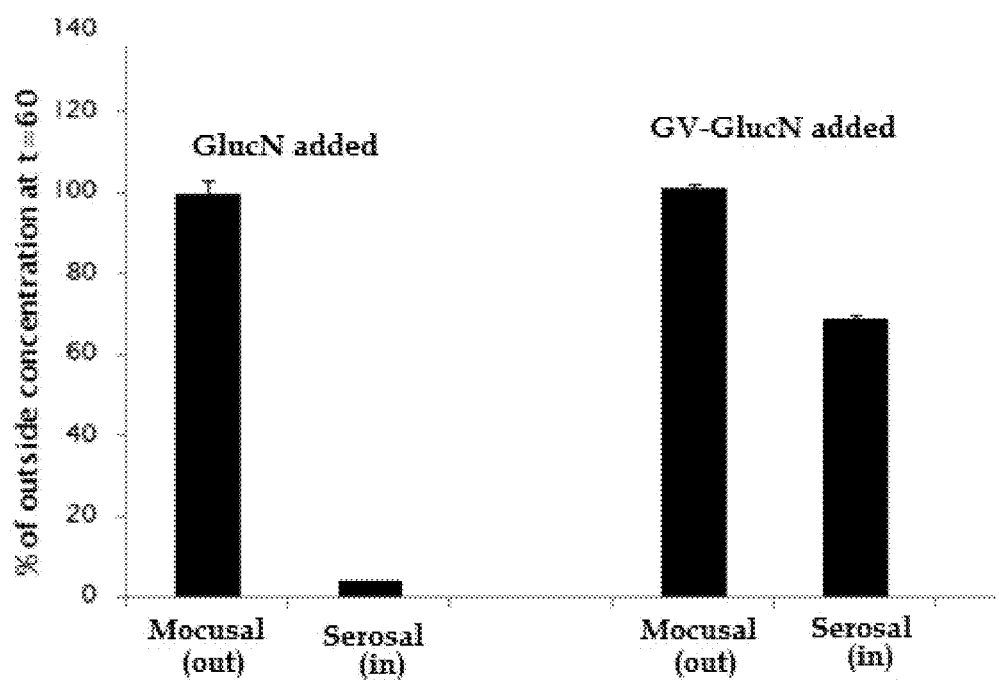
FIG. 4 shows the results, the comparison of absorption of through everted rat gut of GlnC with GV-GlcN.

The present invention is a pro-drug of GlcN with the following properties that render the invention superior to GlcN in both bioavailability and therapeutically beneficial, e.g., effective against adjuvant arthritis, osteoarthritis, and/or rheumatoid arthritis:
(a) Physicochemically stable so that it can be manufactured as easy-to-swallow size tablets;
(b) Relatively stable in the gastrointestinal tract. FIG. 4 shows that GV-GlcN is stable (greater than 96%) after 60 minutes exposure to the gut, that is, GV-GlcN does not convert into glucosamine within the 60 minutes;
(c) Efficient in crossing the gut membrane as the intact pro-drug; see FIGS. 4 and 5.
(d) Efficient conversion to GlcN in the liver, consequently delivering high amounts of GlcN to the systemic circulation. Example 11 shows that the pro-drug (GV-GlcN) converts to glucosamine in about 5 minutes. FIG. 5A shows blood concentration.

The compounds described in the present application are esters and amides with one particular ester having the desire properties as a pro-drug. Compounds described herein are structurally different from those reported in Patent CA 1239636 that may also be filed elsewhere under different number. The compounds reported in Patent CA 1239636 are the ether derivatives of GlcN, one of the secondary alcohol group of GlcN is conjugated to peptide by an ether linkage.

Design and Synthesis of Peptide-GlcN Derivatives

To increase gut absorption, we have synthesized pro-drugs that are designed as peptide-GlcN conjugates. This principle has been used earlier for other structurally different compounds (e.g., (16), U.S. Pat. Nos. 5,831,075; 7,371,809; 4,548,819;4,957,924).

The present invention is a composition comprising a glucosamine pro-drug as the active agent. As used herein, glucosamine pro-drug refers to Gly-Val-COO-GlcN (GV-GlcN) or butyryl glucosamine, and combinations thereof. The composition may also include other ingredients that are commonly used in conventional glucosamine formulations, including but not limited to chondroitin, talcum, lactose, magnesium stearate, binders, fillers, flavors, lubricants, disintegrants, and coatings. The preferred composition is a tablet.

The present invention is also the use of the active agent and/or composition described above for any purpose that provides therapeutic benefit. Examples of therapeutic benefit includes but is not limited to the treatment of osteoarthritis, rheumatoid arthritis, and adjuvant arthritis.

Example 1

Figure 1:
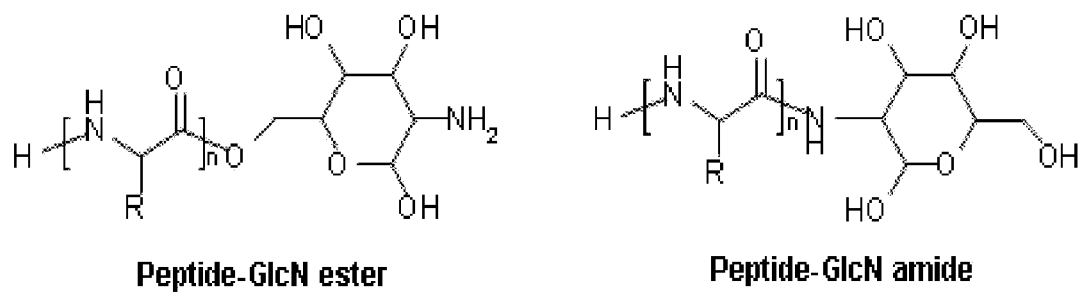
FIG. 1 peptide-GlcN ester and peptide-GlcN amide derivatives.

Of several GlcN functional groups, the primary alcohol and the amine were used to make peptide-GlcN ester and peptide-GlcN amide derivatives, respectively (FIG. 1). Several mono- and di-amino acid derivatives of GlcN, such as, Val-COO-GlcN, Phe-COO-GlcN, Val-CONH-GlcN, Phe-CONH-GlcN, Val-Val-COO-GlcN, Phe-Phe-COO-GlcN, Val-Val-CONH-GlcN, and Phe-Phe-CONH-GlcN, were synthesized.

Example 2

Figure 2:
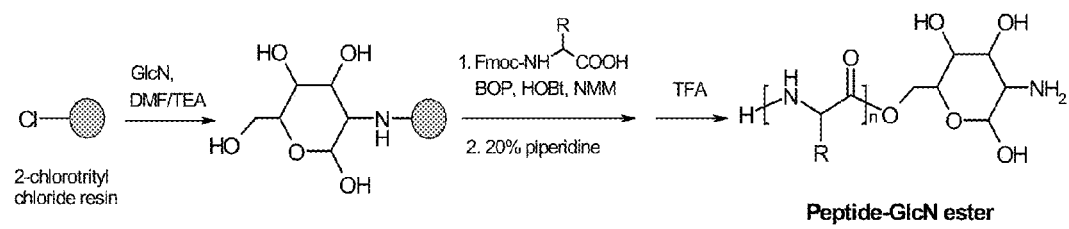
FIG. 2 The peptide-GlcN ester derivatives are synthesized using solid-phase synthesis on a 2-chlorotrityl chloride resin.

The peptide-GlcN ester derivatives were synthesized using solid-phase synthesis on a 2-chlorotrityl chloride resin as described before for other compounds (17,18). As depicted in FIG. 2, in a typical solid phase synthesis, GlcN may be dissolved in dimethylformamide/triethylamine (DMF/TEA) and added to the pre-swelled resin in dichloromethane (DMC). Coupling between the resin and GlcN is achieved by stirring the mixture overnight at room temperature (19). The resin is then drained to remove all the reagents and solvents followed by washing with DMF and DCM.

In the next step, the Fmoc or Boc protected amino acid is activated by the addition of BOP, HOBt, and NMM in DMF. The activated amino acid or dipeptide is then added to the resin and the mixture is stirred for several hours at room temperature. The primary alcohol group of GlcN reacts with the activated carboxylate of the amino acid (or dipeptide). After draining and washing, the resin is treated with 20% piperidine to remove Fmoc from the terminal amino group prior to final cleavage. In the case of Boc protected terminal amino group, the Boc removal is achieved during the final cleavage step.

The final cleavage of the product from the resin is achieved by treating the resin with trifluoroacetic acid (TFA) in DCM. The resulting solution is dried under vacuum, followed by washing with cold ether to obtain the final product. The product may be characterized by mass spectrometry. Some compounds were also characterized by reversed-phase HPLC.

Example 3

The peptide-GlcN amide derivatives were synthesized in solution. Briefly, GlcN is dissolved in DMF/TEA, followed by addition of pre-activated Boc-amino acid or Boc-protected dipeptide as described above for the solid phase synthesis. The resulting mixture is stirred overnight and water is added to precipitate the Boc-protected peptide-GlcN conjugate. The conjugate is then treated with TFA in DCM to remove the Boc-protection, followed by evaporation to dryness. The product is washed with cold ether prior to characterization by mass spectrometry and reversed-phase HPLC.

Example 4

Chemical Stability

Compounds were transferred into transparent glass vials and placed in 60° C. oven for 48 h. Compound with <96% stability are considered unstable.

Example 5

Stability in the Gut

Figure 4A:
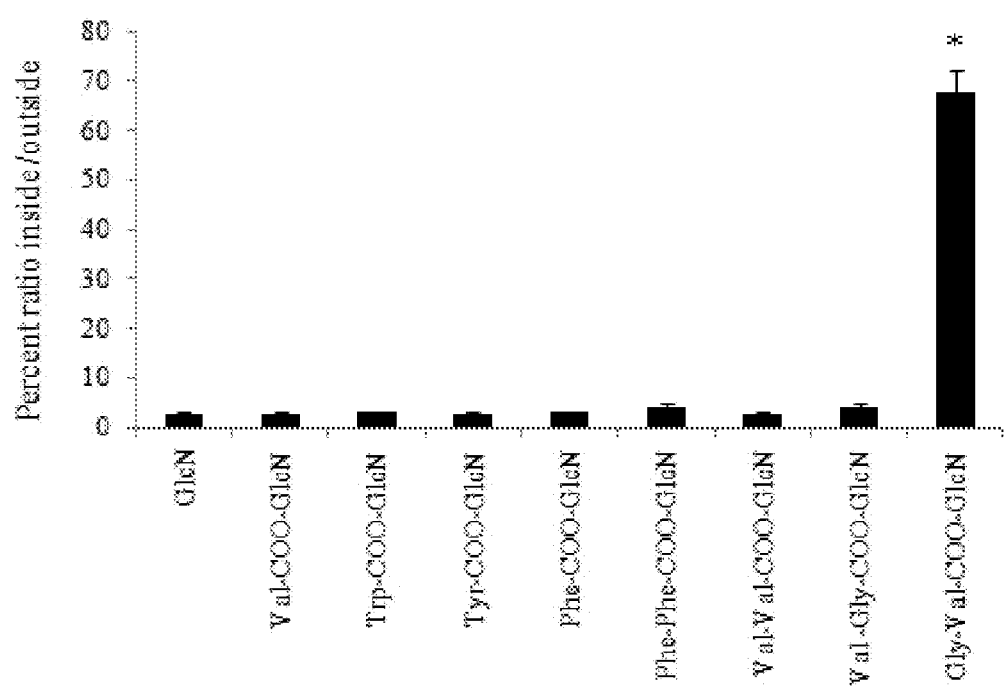
FIG. 4a shows the Average % of ratio of GlcN inside over outside the rat gut sack after 60 min for the ester derivatives of GlcN. Gly-Val-COO-GlcN is GV-GlycN.

Pro-drugs were incubated for 2 h with homogenized rat stomach or intestine while the pH is kept at 1.0 or 7.4, respectively. Samples are taken at 30 min interval for the analysis of the pro-drug and GlcN. This procedure was used as a prerequisite to further tests described in Examples 6, 7 and 8. A compound with low stability under this condition was decided to be unsuitable for further test. FIG. 4 shows the results, the comparison of absorption of through everted rat gut of GlnC with GV-GlcN. Everted rat gut sacks are immersed in 80 µg/mL (GlcN equivalent) of GlucN HCl or GV-GluN HCl solution. The appearance of glucosamine each compound inside the sack (serosal) was measured. FIG. 4A shows the Average % of ratio of GlcN inside over outside the rat gut sack after 60 min for the ester derivatives of GlcN. Gly-Val-COO-GlcN is GV-GlycN.

These comparisons to glucosamine show that the prodrugs of the present invention exhibit greater bioavailability.

Example 6

Hepatic Metabolism

Male Sprague-Dawley rats were sacrificed under anesthesia, their liver were excised and stored at −80° C. before use. Tissues were homogenized in 10 ml of chilled (4° C.) DPBS for about 30 seconds with a tissue homogenizer in an ice bath. Subsequently, the homogenates were centrifuged at 12,500 rpm for 25 min at 4° C. to remove cellular debris and the supernatant was used for hydrolysis studies. The compounds were incubated in the presence of this preparation at 37° C. Samples were collected over time and analyzed using HPLC. Percent of the prodrug converted to GlucN was measured.

Example 7

In Vivo Absorption Through Everted Rat Gut

A mid line incision was made in the anesthetised rat abdomen, the intestine was exposed and five 10 cm segments of the jejunum are cut. In ice cold Krebs Henseleit buffer, the intestinal content are removed and each segment are everted over a glass rod, tied from one side, a polyethylene tube is inserted into the other side and tied. The segments are filled with buffer and incubated in a perfusion apparatus containing oxygenated Krebs Henseleit buffer at 37° C. The test compound was added to the mucosal (outer surface of the everted gut) and serial samples were collected from both sides. The percent of the movement from outside (mucosal) to inside (serosal) was measured and compared (FIG. 4).

In addition to assess the crossing of the compound through the gut wall, the data were used to test the stability of the pro-drug in the presence of viable gut membrane. A lack of presence of GlcN indicated stability and lack of hydrolysis to GlcN. Calculation of mass-balance in both side of the wall was used to account for unchanged Pro-drug, i.e., stability.

Example 8

Bioavailability in the Rat

Prodrugs or GlcN HCl or sulphate were administered to rats in single oral doses equivalent to a fix amount of GlcN. Plasma GlcN concentrations were measured using HPLC in serial sample collected over a period of time. The areas under plasma-concentration-time curves (AUC or relative bioavailability) were calculated and compared (FIGS. 5 and 5a).

Figure 5:
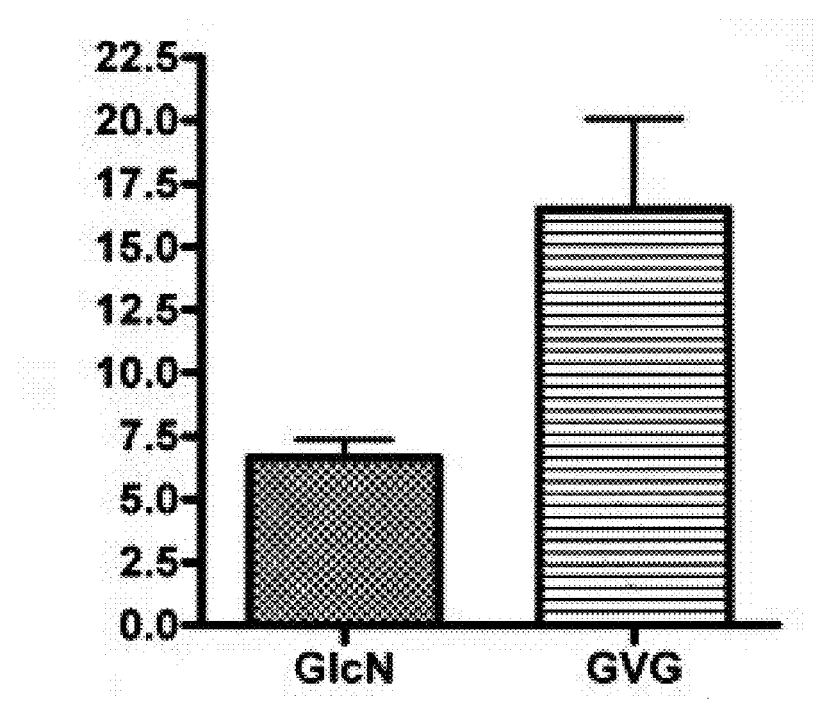
FIG. 5 shows $AUC_{(0-4)}$ (mg.h/L) of GlcN following administration of 110 mg GlcN equivalent of GlcN HCl (GlcN, n=11) and GV-GlcN (GVG, n=7) to rats.
Figure 5A:
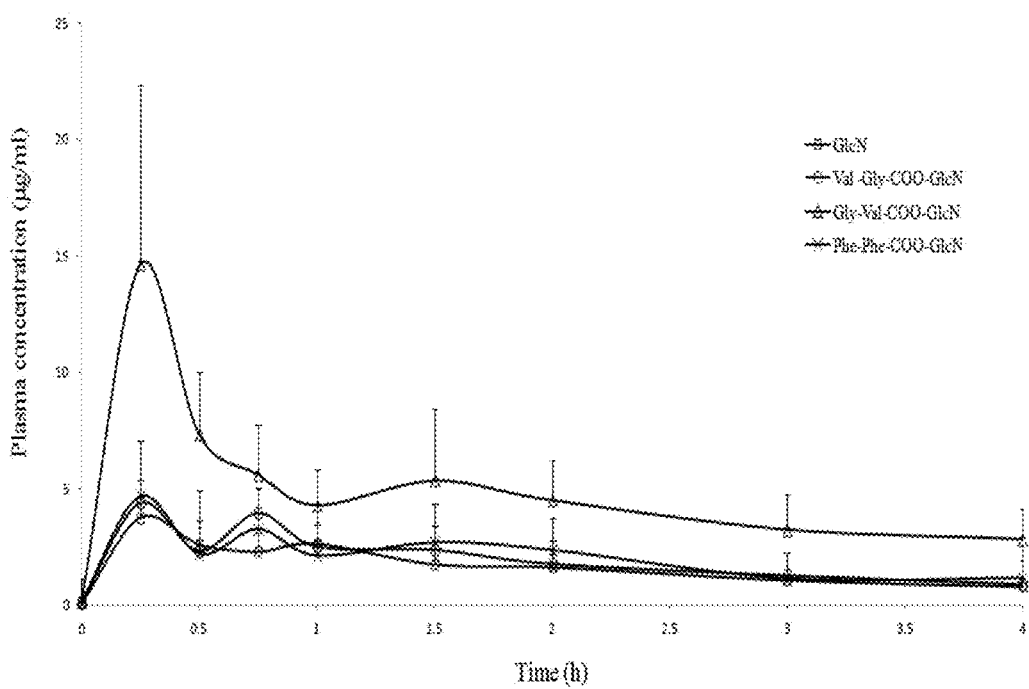
FIG. 5a shows the mean plasma concentration of glucosamine after administration of 110 mg/kg (GlcN equivalent) of GlcN, Gly-Val-COO-GlcN (GV-GlcN), Phe-Phe-COO-GlcN, and Val-Gly-COO-GlcN (GV-GlcN).

FIG. 5 shows $AUC_{(0-4)}$ (mg.h/L) of GlcN following administration of 110 mg GlcN equivalent of GlcN HCl (GlcN, n=11) and GV-GlcN (GVG, n=7) to rats.

FIG. 5A shows the mean plasma concentration of glucosamine after administration of 110 mg/kg (GlcN equivalent) of GlcN, Gly-Val-COO-GlcN (GV-GlcN), Phe-Phe- COO-GlcN, and Val-Gly-COO-GlcN (GV-GlcN). The area under the concentration curve-time was significantly greater than GlcN for GV-GlcN but not for other tested compounds. (n=3-5/group).

Example 8a

Bioavailability in Human

In a randomized fashion GV-GlcN HCl and glucosamine HCl both at 50 mg glucosamine equivalent were orally administered to a healthy male volunteer. The compounds were dispensed in identical capsules which were administered three days apart. As a measure of relative bioavailability, the total urine output were collected for 8 hours and glucosamine measured therein.

Example 9

Efficacy Against Adjuvant Arthritis

Under anesthesia, rats were injected with 0.2 ml of 50 mg/ml *Mycobacterium butyricum* suspended in squalene in the base of the tail (day 0). Their paw thickness was measure daily. Within 12-14 days significant increases in paw thickness were noticed, indicative of the emergence if adjuvant arthritis. Repeated daily doses of drugs were administered either right after the time of *Mycobacterium* injection (to prevent emergence of arthritis) or after the appearance of arthritis (to treat arthritis). Animals were monitored for their arthritis status during the entire length of the experiment.

Example 10

Screening

Amide and esters synthesized as listed in Appendix 1 were tested for their suitability as GlcN pro-drug. Except for one, all of the tested pro-drugs failed at one or more set criteria explained under Summary on Invention. They possessed either no or little stability in the presence of excised gut or did not convert to GlcN when exposed to the rat liver.

Example 11

GV-GlycN

Figure 3:
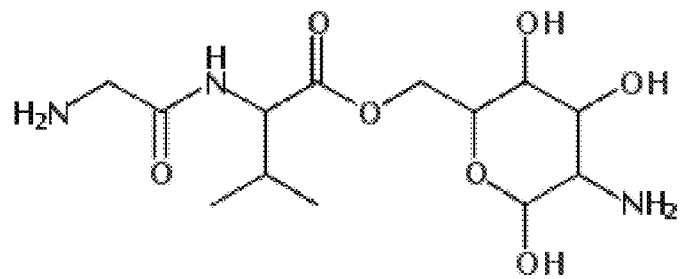
FIG. 3 The glycine-valine sequence used for (5-amino-3,4,6-trihydroxyoxan-2-yl)methyl 2-(2-aminoacetamido)-3-methylbutanoate or glycine-valine-COO-GlcN (GV-GlcN)

The glycine-valine sequence used for (5-amino-3,4,6-trihydroxyoxan-2-yl)methyl 2-(2-aminoacetamido)-3-methylbutanoate or glycine-valine-COO-GlcN (GV-GlcN) (FIG. 3) surprisingly exhibited acceptable prodrug characteristics as described above in the Summary. GV-GlcN is physicochemically stable as measured according to Example 4; >96% stable at 60° C. for 48 h); it is relatively stable when incubated in the presence of rat gut as measured according to Example 5; t1/2 of decomposition >16 h)); it is readily converted to GlcN by homogenised liver preparations as tested according to Example 6; Complete hydrolysis to GlcN in <5 min); it crosses everted rat gut as measured according to Example 7; ~80% transport As depicted in FIG. 5, the mean area under plasma concentration-time curve (AUC, bioavailability) of GlcN in rat plasma following administration of GV-GlcN (110 mg GlcN equivalent) was significantly and substantially greater than that following administration of GlcN HCl (110 mg GlcN equivalent). This result can be extrapolated to GlcN sulfate as well since equal AUC values have been were observed for GlcN following oral administration of its HCl and sulphate salt (23).

In a human subject, the cumulative amount of glucosamine in 0-8 hour urine (relative bioavailability) following the administered oral doses of glucosamine and GV-GlcN was 1.32 and 3.17 mg, respectively, indicating a substantial increase in the bioavailability of glucosamine following oral administration of GV-GlcN as compared with glucosamine.

Efficacy.

Figure 6:
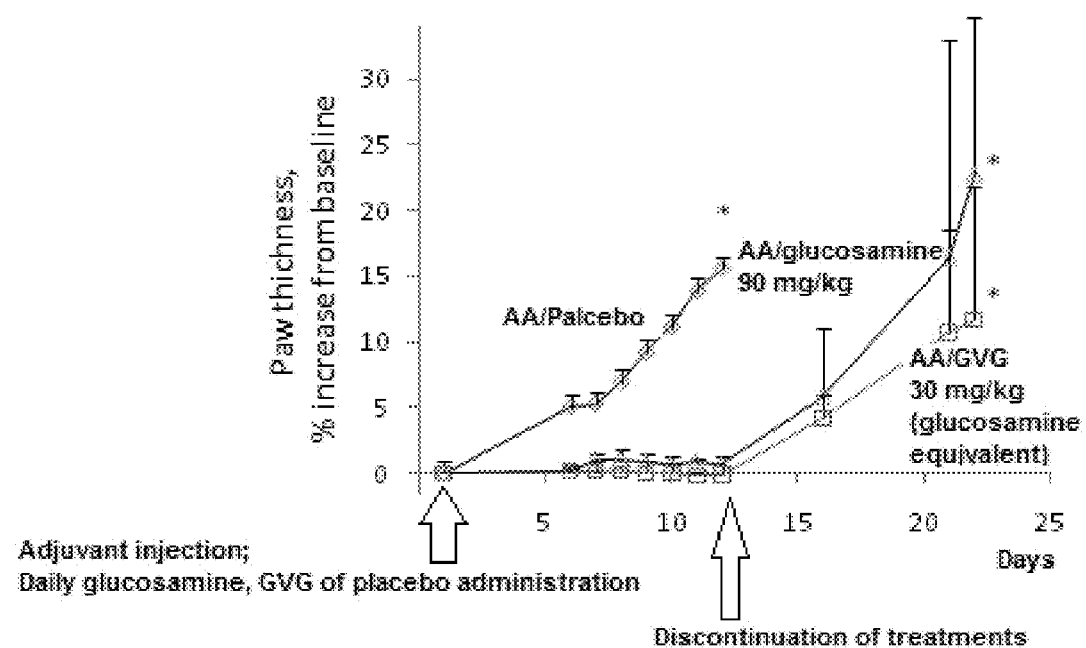
In FIG. 6, Preventing effect of GlcN HCl (90 mg glucosamine equivalent) and GV-GluN (GVG) (30 mg glucosamine equivalent) on the emergence of AA caused by *Mycobacterium butyricum*.
Figure 7:
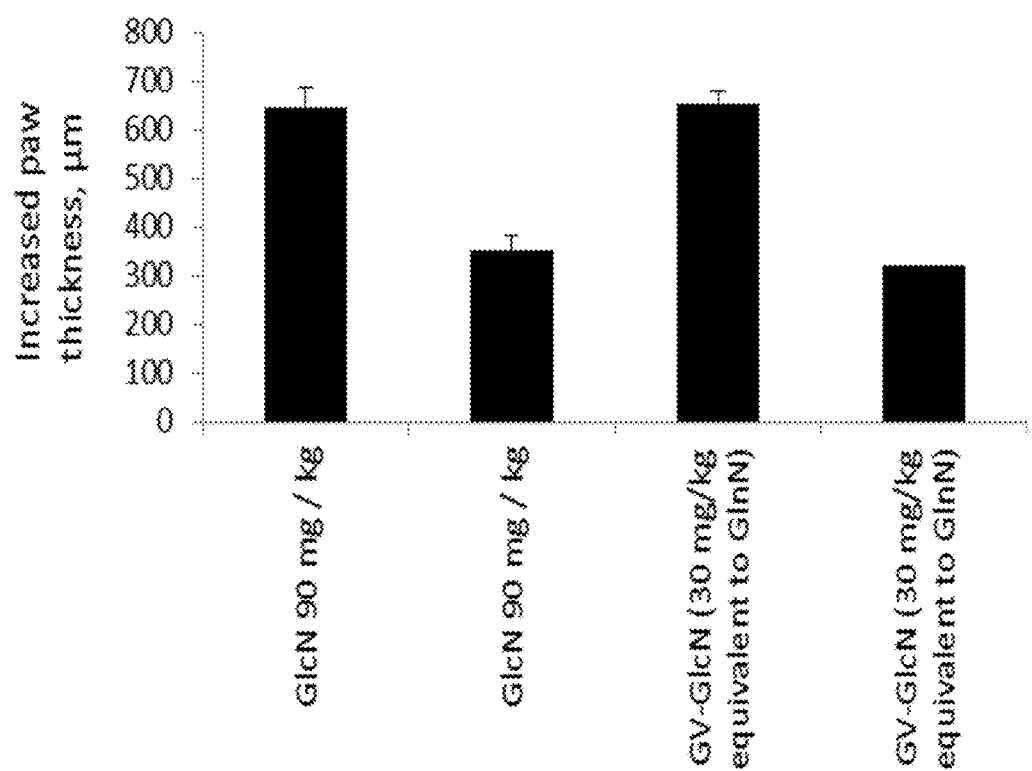
In FIG. 7, Significant (p>0.05) reduced paw thickness following four days of daily doses of GlcN HCl (90 mg glucosamine equivalent) or GV-GluN (30 mg glucosamine equivalent).

As depicted in FIGS. 6 and 7, GV-GlcN is three fold more potent than GlcN in preventing or controlling the emergence of adjuvant arthritis (AA).

On day zero, *Mycobacterium butyricum* is injected to all rats along with daily doses of glucosamine, GV-GlnN or placebo. The placebo group develops severe AA but not the ones that received either treatment. Upon discontinuation of the treatments, AA emerges (FIG. 6). The preventive effect parallels that of treatment effect after emergence of AA since treatment for four days with daily doses of either 90 mg/kg GlcN or 30 mg/kg (GlcN equivalent) GV-GlcN significantly reduce the paw thickness enlarged by AA (FIG. 7).

In FIG. 6, Preventing effect of GlcN HCl (90 mg glucosamine equivalent) and GV-GluN (GVG) (30 mg glucosamine equivalent) on the emergence of AA caused by *Mycobacterium butyricum*. The data suggest i) placebo-treated animals develop arthritis; ii) both GlcN and GV-GlcN prevent the disease; iii) a 3-fold greater potency for GV-GlcN as compared with GlcN (30 mg vs 90 mg GlcN equivalent). Keys: AA, adjuvant arthritis; CVG, GV-GlvN. (* denotes significant change from baseline.)

In FIG. 7, Significant (p>0.05) reduced paw thickness following four days of daily doses of GlcN HCl (90 mg glucosamine equivalent) or GV-GluN (30 mg glucosamine equivalent). The treatments commenced 14 days following injection of by *Mycobacterium butyricum* when pawthickness had significantly increased. Equal effectiveness of the two treatments suggests a 3-fold greater potency for GV-GlcN as compared with GlcN (30 mg vs 90 mg GlcN equivalent).

Example 12

Chemical structures of synthesized, characterized, and tested Pro-drugs. Amino acids are abbreviated as Ala, alanine; Asp, aspartic acid; Gly, glycine; Phe, phenylalanine; Val, valine; Trp, tryptophan; Tyr, tyrosine.

Peptide-GlcN Ester Pro-Drugs

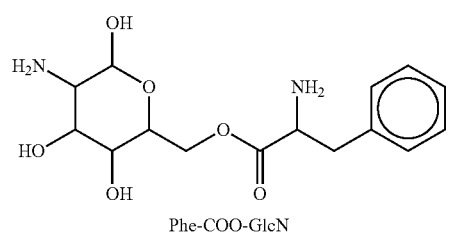

Phe-COO-GlcN

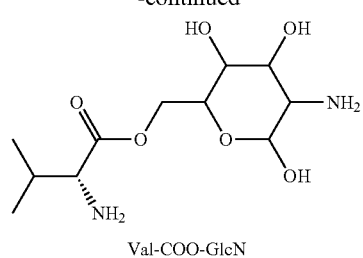

Val-COO-GlcN

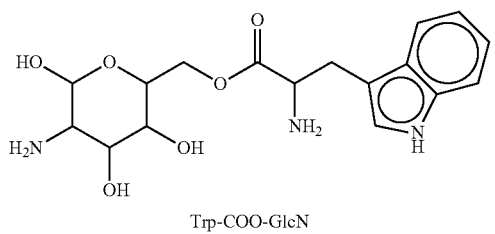

Trp-COO-GlcN

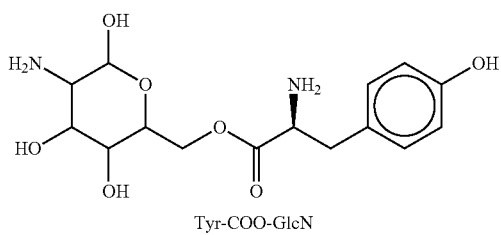

Tyr-COO-GlcN

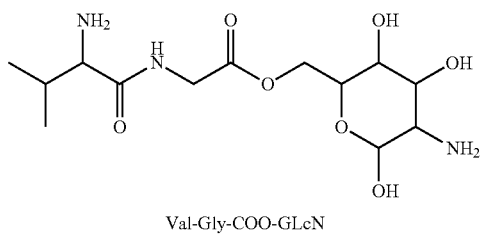

Val-Gly-COO-GLcN

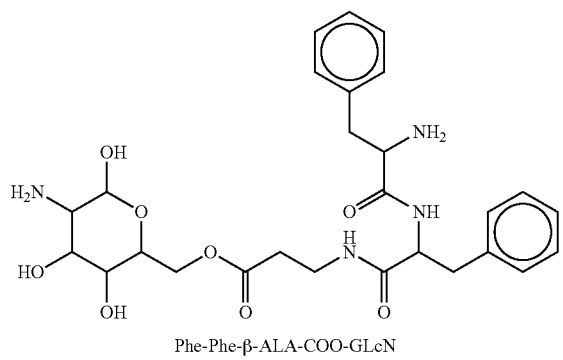

Phe-Phe-β-ALA-COO-GLcN

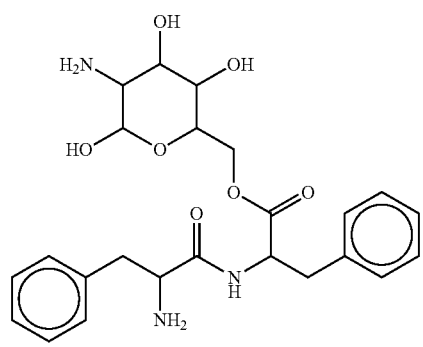

Phe-Phe-COO-GlcN

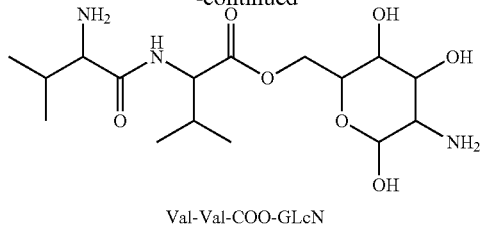

Val-Val-COO-GLcN

Example 13

Chemical structures of synthesized, characterized, and tested Pro-drugs. Amino acids are abbreviated as Ala, alanine; Asp, aspartic acid; Gly, glycine; Phe, phenylalanine; Val, valine; Trp, tryptophan; Tyr, tyrosine.

Peptide-GlcN Amide Pro-Drugs

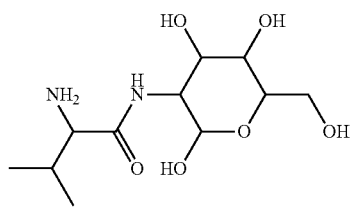

Phe-CONH-GlcN

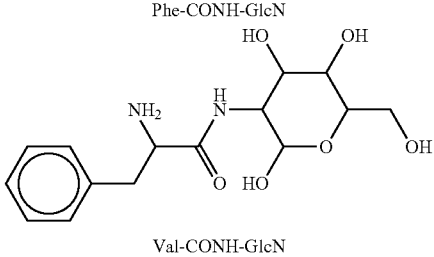

Val-CONH-GlcN

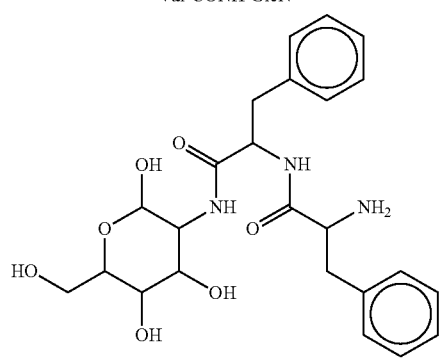

Phe-Phe-CONH-GlcN

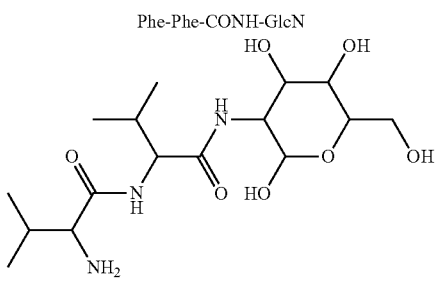

Val-Val-CONH-GlcN

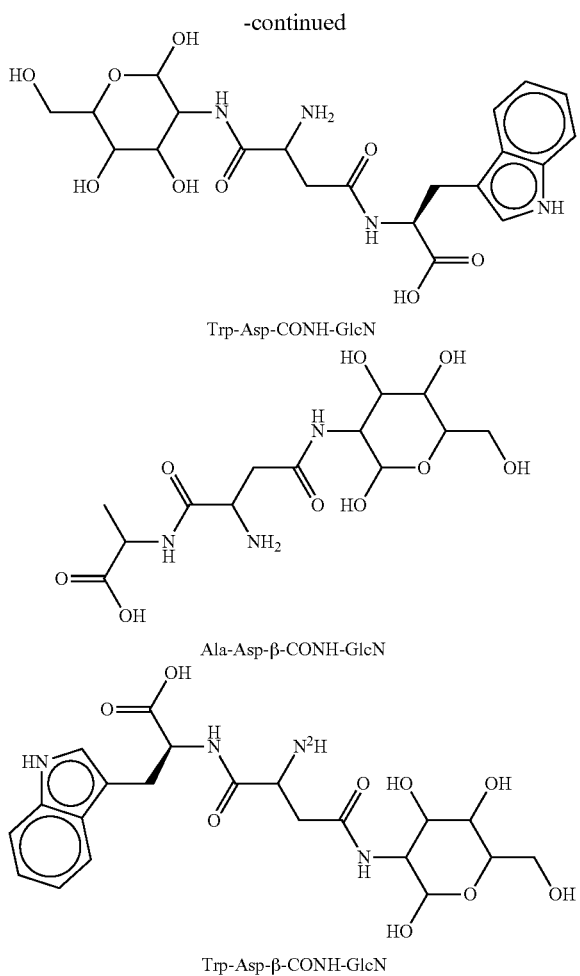

Trp-Asp-CONH-GlcN

Ala-Asp-β-CONH-GlcN

Trp-Asp-β-CONH-GlcN

REFERENCES (1) Richy F, Bruyere O, Ethgen O, Cucherat M, Henrotin Y, Reginster J Y. Structural and symptomatic efficacy of glucosamine and chondroitin in knee osteoarthritis: a comprehensive meta-analysis. Arch Intern Med 2003 Jul. 14; 163 (13):1514-22.

(2) Towheed T E, Anastassiades T. Glucosamine therapy for osteoarthritis: an update. J Rheumatol 2007 September; 34(9):1787-1790.

(3) Wandel S, Juni P, Tendal B, Nuesch E, Villiger P M, Welton N J, et al. Effects of glucosamine, chondroitin, or placebo in patients with osteoarthritis of hip or knee: network meta-analysis. BMJ 2010 Sep. 16; 341:c4675.

(4) Bruyere O, Pavelka K, Rovati L C, Gatterova J, Giacovelli G, Olejarova M, et al. Total joint replacement after glucosamine sulphate treatment in knee osteoarthritis: results of a mean 8-year observation of patients from two previous 3-year, randomised, placebo-controlled trials. Osteoarthritis Cartilage 2008 February; 16(2):254-60.

(5) Sawitzke A D, Shi H, Finco M F, Dunlop D D, Bingham C O, 3rd, Harris C L, et al. The effect of glucosamine and/or chondroitin sulfate on the progression of knee osteoarthritis: a report from the glucosamine/chondroitin arthritis intervention trial. Arthritis Rheum 2008 October; 58(10): 3183-91.

(6) Hughes R, Carr A. A randomized, double-blind, placebo-controlled trial of glucosamine sulphate as an analgesic in osteoarthritis of the knee. Rheumatology (Oxford) 2002 March; 41(3):279-284.

(7) Cibere J, Thorne A, Kopec J A, Singer J, Canvin J, Robinson D B, et al. Glucosamine sulfate and cartilage type II collagen degradation in patients with knee osteoarthritis: randomized discontinuation trial results employing biomarkers. J Rheumatol 2005 May; 32(5):896-902.

(8) Cibere J, Kopec J A, Thorne A, Singer J, Canvin J, Robinson D B, et al. Randomized, double-blind, placebo-controlled glucosamine discontinuation trial in knee osteoarthritis. Arthritis Rheum 2004 Oct. 15; 51(5):738-745.

(9) Vlad S C, LaValley M P, McAlindon T E, Felson D T. Glucosamine for pain in osteoarthritis: why do trial results differ? Arthritis Rheum 2007 July; 56(7):2267-77.

(10) Greenwald R A. Marginal efficacy of glucosamine: comment on the article by VLAD et al and the editorial by Reginster. Arthritis Rheum 2008 January; 58(1):332; author reply 333-4.

(11) Aghazadeh-Habashi A, Sattari S, Pasutto F, Jamali F. Single dose pharmacokinetics and bioavailability of glucosamine in the rat. J Pharm Pharm Sci 2002 May-August; 5(2):181-4.

(12) Hua J, Suguro S, Hirano S, Sakamoto K, Nagaoka I. Preventive actions of a high dose of glucosamine on adjuvant arthritis in rats. Inflamm Res 2005 March; 54(3):127-32.

(13) Jackson C G, Plaas A H, Sandy J D, Hua C, Kim-Rolands S, Barnhill J G, et al. The human pharmacokinetics of oral ingestion of glucosamine and chondroitin sulfate taken separately or in combination. Osteoarthritis Cartilage 2009 Nov. 10.

(14) Persiani S, Roda E, Rovati L C, Locatelli M, Giacovelli G, Roda A. Glucosamine oral bioavailability and plasma pharmacokinetics after increasing doses of crystalline glucosamine sulfate in man. Osteoarthritis Cartilage 2005 December; 13(12):1041-9.

(15) Russell A S, Aghazadeh-Habashi A, Jamali F. Active ingredient consistency of commercially available glucosamine sulfate products. J Rheumatol 2002 November; 29(11):2407-9.

(16) Bai J P, Hu M, Subramanian P, Mosberg H I, Amidon G L. Utilization of peptide carrier system to improve intestinal absorption: targeting prolidase as a prodrug-converting enzyme. J Pharm Sci 1992 February; 81(2):113-116.

(17) Beleid R, Douglas D, Kneteman N, Kaur K. Helical peptides derived from lactoferrin bind hepatitis C virus envelope protein E2. Chem Biol Drug Des 2008 November; 72(5):436-443.

(18) Kaur K, Andrew L C, Wishart D S, Vederas J C. Dynamic relationships among type IIa bacteriocins: temperature effects on antimicrobial activity and on structure of the C-terminal amphipathic alpha helix as a receptor-binding region. Biochemistry 2004 Jul. 20; 43(28):9009-9020.

(19) Thieriet N, Guibe F, Albericio F. Solid-phase peptide synthesis in the reverse (N→C) direction. Org Lett 2000 Jun. 29; 2(13):1815-1817.

(20) Shayeganpour A, El-Kadi A O, Brocks D R. Determination of the enzyme(s) involved in the metabolism of amiodarone in liver and intestine of rat: the contribution of cytochrome P450 3A isoforms. Drug Metab Dispos 2006 January; 34(1):43-50.

(21) Berry B W, Jamali F. Presystemic and systemic chiral inversion of R-(-)-fenoprofen in the rat. J Pharmacol Exp Ther 1991 August; 258(2):695-701.

(22) Anand B S, Katragadda S, Mitra A K. Pharmacokinetics of novel dipeptide ester prodrugs of acyclovir after oral administration: intestinal absorption and liver metabolism. J Pharmacol Exp Ther 2004 November; 311(2):659-67.

(23) Ali Aghazadeh-Habashi, Fakhreddin Jamali The Glucosamine Controversy; A Pharmacokinetic Issue. J Pharm Pharm Sci, 2011, 14: 264-73.

We claim:

1. A composition comprising a pharmaceutically acceptable salt or base of compounds chemically containing glucosamine (GlcN) with one or more amino acids attached at the amino or alcohol groups to form amide or ester of the amino-sugar with no ether linkage, wherein said compound is selected from the group consisting of a pharmaceutically accepted salt or base of (5-amino-3,4,6-trihydroxyoxan-2-yl) methyl 2-(2-aminoacetamido)-3-methylbutanoate; a pharmaceutically accepted salt or base of glycine-valine-COO-GlcN (GV-GlcN); and combinations thereof.

2. The pharmaceutical composition of claim 1 wherein the acidic salts are hydrochloride and sulfate.

3. A method of treating any disease or condition for which glucosamine has been previously prescribed comprising administering an effective amount of a glucosamine pro-drug comprising a pharmaceutically accepted salt or base of (5-amino-3,4,6-trihydroxyoxan-2-yl)methyl 2-(2-aminoacetamido)-3-methylbutanoate or a pharmaceutically accepted salt or base of glycine-valine-COO-GlcN (GV-GlcN); or combinations thereof.

4. The method of claim 3 wherein the disease or condition is selected from the group consisting of osteoarthritis, rheumatoid arthritis, and adjuvant arthritis.

* * * * *